United States Patent [19]
Madsen

[11] 4,246,486
[45] Jan. 20, 1981

[54] X-RAY PHOTOGRAPHY DEVICE
[75] Inventor: Knud Madsen, Jaerfaella, Sweden
[73] Assignee: Siemens Aktiengesellschaft, Berlin & Munich, Fed. Rep. of Germany
[21] Appl. No.: 19,452
[22] Filed: Mar. 12, 1979
[30] Foreign Application Priority Data
Apr. 20, 1978 [DE] Fed. Rep. of Germany ....... 2817391
[51] Int. Cl.³ ...................... G01N 21/00; G01N 23/00
[52] U.S. Cl. .................................... 250/491; 250/511; 354/165
[58] Field of Search ................. 250/491, 511; 356/17, 356/3, 19, 16, 1; 354/165

[56] References Cited
U.S. PATENT DOCUMENTS 1,976,179  10/1934  Mannl ................................... 250/491
2,659,824  11/1953  Burnham ............................. 250/491
4,092,544  5/1978  Grim .................................... 250/491

Primary Examiner—Alfred E. Smith
Assistant Examiner—Thomas P. O'Hare
Attorney, Agent, or Firm—Hill, Van Santen, Steadman, Chiara & Simpson

[57] ABSTRACT

A focus alignment system for X-ray photography devices is provided for use with such devices where the film holder is independent of the X-ray source. The X-ray source has associated therewith two light beam projectors. The beam of one light projector is aligned with the X-ray beam while the beam of the other projector is at an angle thereto. The X-ray beam focus to film distance is correctly set when the light beams intersect on the surface of the film holder. Markings on the film holder indicate central positioning of the X-ray beam when the one light beam is aligned with the markings.

17 Claims, 10 Drawing Figures

U.S. Patent
Jan. 20, 1981
4,246,486
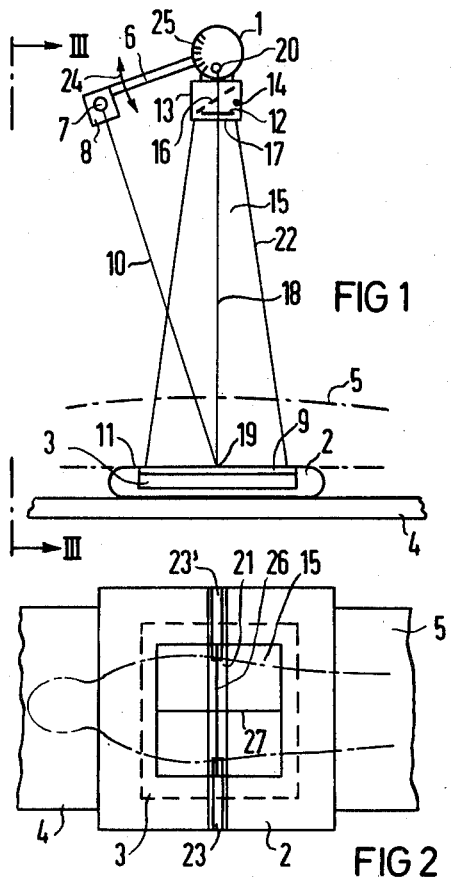
FIG 1
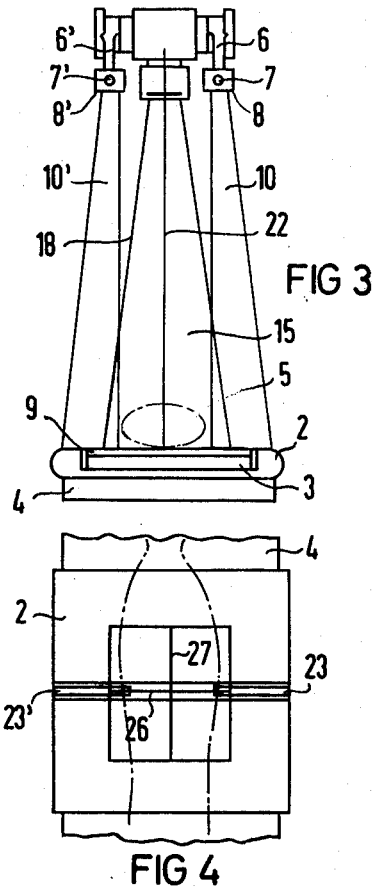
FIG 3
FIG 2
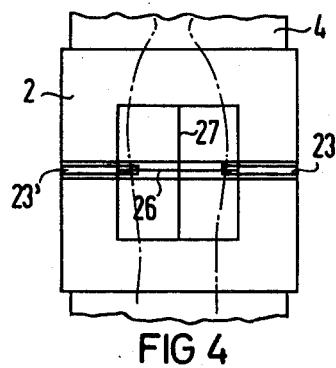
FIG 4
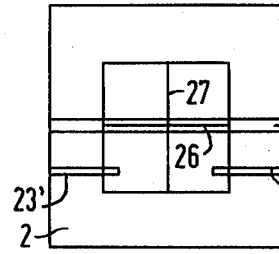
FIG 5
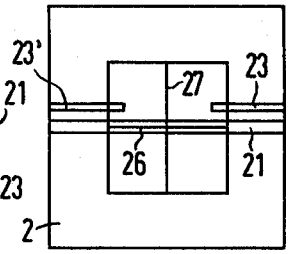
FIG 6
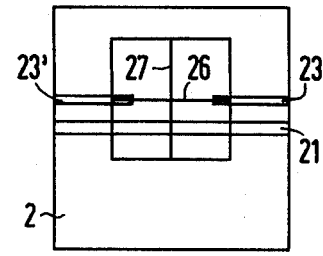
FIG 7
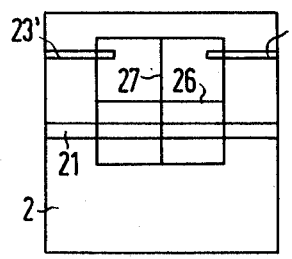
FIG 8
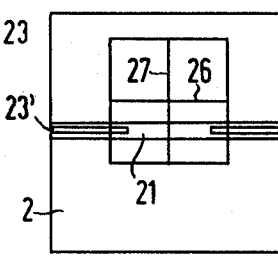
FIG 9
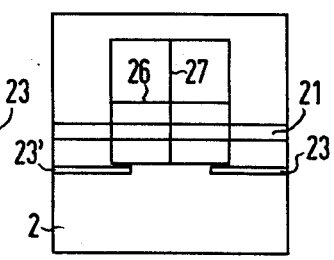
FIG 10

X-RAY PHOTOGRAPHY DEVICE

BACKGROUND OF THE INVENTION

1. Field of the Invention

This invention relates to X-ray photographic devices.

2. Prior Art

The invention is directed to X-ray photographic devices having an X-ray tube equipped with a primary diaphragm for defining the X-ray beam and having a film holder or cassette which is moveable independently of the X-ray tube in any desired direction. The X-ray tube primary diaphragm limits the X-ray beam. At least one light beam source is spatially rigidly locatd with respect to the primary diaphragm and the X-ray tube. The light beam from that source is focused and is provided with means for limiting the light beam. A marking on the film cassette or on a component attached to the cassette, is designed such that by projecting the light beam properly with respect to the marking, an operator can determine whether the central beam of the X-ray will impinge upon the center of the film holder and whether the desired X-ray focus to film distance exists.

X-ray photographic devices of the above described type are primarily used in connection with bedridden patients. In such assemblies the X-ray apparatus is mobile, generally being wheel mounted. An independent film cassette is positioned underneath or adjacent the patient. Generally such devices are provided with a swing arm which carries the X-ray tube. Thus the X-ray tube can be readily positioned relative to the patient and, for adjustment of the beam, relative to the cassette. For the taking of X-rays, it is also known to use secondary beam rasters in order to reduce secondary radiation. Such rasters may, for example, consist of lead laminae positioned on edge and having a high X-ray beam absorption ability. The lead laminae may be surrounded by a medium having a low absorption. The raster assembly is then positioned between the patient and the film. This requires a specific film to focus distance for the specific raster being used. If the film to focus distance is not correctly adjusted, and if the center of the X-ray beam is not positioned properly with respect to the center of the raster, the picture providing X-radiation may be absorbed by the laminae along the width of the secondary radiation and a so-called raster effect formed. This raster effect is very interfering in practice and often requires, particularly with bedridden patients, the repetition of the taking of the X-ray photograph. This brings about an increased patient dosage of radiation, increased film consumption, and a waste of hospital personnel.

Therefore devices which provide for alignment of the film to focus distance and of the beam center of film center positioning have the ability to substantially reduce such disadvantages. A device having these capabilities as above described is known from U.S. Pat. No. 4,092,544, issued May 30, 1978, the teachings of which are herein incorporated by reference. In that construction the film holder or cassette is provided with a rigid laterally projecting portion. A marking is applied to that projecting portion. The marking includes a rectangular field. A light source rigidly positioned with respect to the X-ray tube has its light beam rectangularly limited. According to the teachings of that patent, the limited light beam is, prior to taking the X-ray, adjusted such that the marking on the cassette projection coincides with the rectangular light beam projection. When that occurs, the central beam of the X-ray will be aligned with the center of the film holder. Moreover the focus to film distance will also be correctly adjusted.

Although the above described device has the capability of eliminating many of the above-mentioned disadvantages, it has a noticeable disadvantage in that the rectangular marking on the cassette is relatively small such that it is difficult and time consuming to correctly adjust the light beam relative thereto. It would therefore be an improvement in the art to provide a simplified manner of properly locating the X-ray source with respect to the film in devices where the film is moveable independent of the X-ray source and is not fixed thereto.

SUMMARY OF THE INVENTION

It is therefore the principal object of this invention to provide an X-ray photographic device of the above described type in which the distance between the film cassette and the X-ray tube (focus to film distance) can be simply and readily adjusted.

This principal objective is met by providing at least one light source aligned with the X-ray tube and the primary diaphragm and a second light source spaced therefrom and projecting at an angle thereto such that the light radiation and/or light beam shadows from the two sources intersect at an angle at a point spaced from the X-ray tube. By properly positioning the light sources, when the intersecting beams, or beam and shadow, occur in connection with markings on the film holder, the distance from the intersecting beam's point of intersection on the film holder to the X-ray focus will be the proper film to focus distance for the raster employed. Thus, the focus to film distance can be easily adjusted simply by bringing the two light beams into coincidence on the film holder.

In a particularly advantageous embodiment of the invention, the film holder is provided with markings which are aligned with the center of the film holder, or of the film carried by the film holder or cassette. By aligning the markings with the vertex or point of intersection of the light beams, it will be assured that the X-ray beam is properly aligned with respect to the center of the film. This is accomplished simultaneously with setting the film to focus distance by having the vertex, which signifies proper film to focus distance setting, used as the point of alignment with the marking on the cassette.

In another modification of the invention, the intersecting light source, which is projected at an angle to the central light beam aligned with the X-ray tube, is housed at the end of one or more swing arms projecting from the central X-ray tube housing. By movement of the swing arms, the vertex or point of intersection with the light beam originating from the central X-ray housing will be changed. By presetting selected lockable positions of the swing arm, different film to focus distances can be selected.

It is therefore an object of this invention to provide an improved method of setting the film to focus distance in X-ray devices having independently moveable film holders.

It is another, and more important object of this invention to provide a device for setting the film to focus distance in X-ray devices having independently moveable film holders by use of projected light beams originating from the X-ray tube member, the beams intersecting at an angle at a point spaced from the tube, the point of intersection, when focused on the film holder, indicating proper film to focus distance.

It is yet another object of this invention to provide a device for setting the film to focus distance in X-ray devices having independently moveable film holders by intersecting two projected light beams originating in fixed relationship relative to the X-ray source, on the surface of a film holder, one of the light beams being aligned with the central beam of the X-ray and being useable to determine central positioning of the film relative to the X-ray beam.

Other objects, features and advantages of the invention will be readily apparent from the following description of a preferred embodiment thereof, taken in conjunction with the accompanying drawings, although variations and modifications may be effected without departing from the spirit and scope of the novel concepts of the disclosure and in which:

BRIEF DESCRIPTION OF THE DRAWINGS

FIG. 1 is a diagrammatic descriptive drawing of an X-ray device according to this invention.

FIG. 2 is a top plan view of the film holder of FIG. 1 illustrating the intersection of the light beams and film holder markings.

FIG. 3 is a view similar to FIG. 1 taken along the lines III-III of FIG. 1.

FIG. 4 is a view similar to FIG. 2 taken at right angles thereto.

FIGS. 5-10 are diagrammatic top elevational views of the film holder showing various misaligned light beam intersection positions.

DESCRIPTION OF THE PREFERRED EMBODIMENT

FIGS. 1 and 3 diagrammatically illustrate an X-ray photographic device according to this invention. The device includes an X-ray housing 1 which contains an X-ray source 20. The housing may be mounted to a wheeled floor stand (not shown). The device further includes a film cassette holder 2 comprising a film cassette 3 positioned in the holder 2, the cassette being inserted between an examination table 4 and a patient 5. The patient is illustrated by the broken lines 5. A secondary beam raster 9 is positioned above the cassette 3 within the holder 2 and underlies the patient 5.

Light sources 7,7' are fixedly carried by the housing 1 and, in the preferred embodiment illustrated, are located at the ends of swing arms 6,6' in housings 8,8'. Only one light 7 is shown in FIG. 1 arranged in a housing 8 at the end of arm 6 extending outwardly from the housing 1. Preferably the light sources 7,7' are provided with well known optics capable of producing bar-shaped light beams 23,23' on the surface 11 of cassette holder 2. The surface 11 is X-ray permeable. The paths of beam projections from the light 7,7' are illustrated as 10,10'.

Housing 13 carried by tube housing 1 contains a primary diaphragm 12 for limiting the X-ray beam. Additionally, positioned within the housing 13 is a light source 14 which is projected through the diaphragm 12 via a reflector 16. Thus, the projection of the light beam 18 from the light source 14 will be aligned with the X-ray beam from the X-ray focus 20. A plate 17 which is light and X-ray permeable is positioned in the primary diaphragm housing 13 and has formed thereon centrally thereof, a cross or other "X" marking which is impermeable to light radiation. Thus, the shadow of the cross will be projected onto the patient 5 and, to the extent that the beam 18 projects beyond the sides of the patient, onto the projecting portions of the holder 2 which also extend beyond the patient's sides. Since the light beam 18 is aligned with the X-ray beam, by maintaining the cross of the plate 17 central of the X-ray beam, it can be assured that the intersecting lines 26,27 of the shadow formed by the cross will indicate the central point for the X-ray beam.

From FIG. 1, it will be apparent that the beam 10 and the beam 18, due to the relative angulation thereto will intersect at an acute angle at a vertex 19. The distance from the vertex 19 to the focus 20 of the X-ray tube is chosen such that when the vertex 19 is reproduced on the surface 11 of the holder 2, the desired focus to film distance will be set for the particular secondary beam raster 9 being used. Preferably the distance of the vertex 19 from the focus 20 will be smaller than the desired focus to film distance by the distance of the film within the cassette 3 from the surface 11.

As illustrated in FIG. 2, the holder 2 is provided with a line mark 21 which extends outwardly from the center of the film area in the holder. If the shadow mark 26 of the cross formed on plate 17 is aligned with the mark 21, and if the light bars 23,23' produced by beams 10,10' are simultaneously aligned with the mark 21, both the focus to film distance will be correctly set and the X-ray beam will be aligned with the center of the film.

In order to provide for this alignment, both the holder 2, the markings 21, the light beam 18 and the beams 10,10' extend outwardly beyond the sides of the patient 5.

As shown in FIGS. 3 and 4, by providing light source assemblies 6,6',7,7',8,8' adjacent each end of the housing 1 of the X-ray tube, the light sources 7,7' will produce parallel beams 10,10',projecting onto the cassette holder 2. The beams 10,10' produce light bars 23,23' which are alignable with the marking 21 of the film holder and with the cross bar 26 of the shadow of the light beam 18. By projecting the cross bars 26,27 on the patient 5, within the field 15 of light beam 18, the X-ray center 22 can be aligned properly on the patient. Moreover by extending the field 15, the line 26 and the light bars 23,23' beyond the sides of the patient, the cross bar 26 and the light bars will be projected onto the holder 2. By aligning both the cross bar 26 and the light bars 23,23' with the markings 21, it will be assured that both proper X-ray alignment and film to focus distance has been achieved.

FIGS. 5-10 show incorrect adjustments of the X-ray tube vis-a-vis the holder 2.

Thus, in FIG. 5, the film to focus distance is too short as is indicated by the light beams 10,10' impinging upon the cassette holder 2 below the shadow mark 26 of the light beam 18. Light marks 23,23' therefore are underneath the line mark 21 of the holder. In this illustrated embodiment the X-ray beam is properly centered as indicated by the fact that shadow line 26 is aligned with the line mark 21 of the holder.

In FIG. 6 the focus to film distance is too long, as is indicated by the light beams 23,23' impinging on the holder above the shadow marking 26. Again in FIG. 6 the X-ray beam is properly centered with respect to the holder 2.

In FIG. 7, the film to focus distance is properly set, however the X-ray beam has not been centered. Film to focus distance is correct because the light bars 23,23' intersect with the shadow mark 26. However centering of the holder 2 is improper since the marking 21 of the holder is below both the light bars 23,23' and the shadow 26.

In FIG. 8 the film to focus distance is too great and the X-ray beam is not centered. In FIG. 9 the film to focus distance is too short, since the light bars 23 are below the shadow 26 and the X-ray tube is not centered. The fact that the light bars 23 are centered with the marking 21 does not alter the mis-setting since for the X-ray beam to be centered, the shadow 26 must be aligned with the marking 21.

In FIG. 10 the film to focus distance is too short and the X-ray beam is not centered.

According to this invention the arms 6,6' of the light source arrangements 6,7,8, and 6',7',8' can be pivotally attached to the housing and be moveable in the direction of the arrows 24. By changing the pivoted position of the light source 7, the angle of incidence of the beam 10 with the beam 18 is changed thereby changing the vertex 19. Thus the light source 7 can be repositioned to increase or decrease the film to focus distance as desired. Scales 25 may be provided on the housing 1 for proper adjustment of the pivoting position of the arms 6,6'. In this manner secondary beam rasters having different film to focus distances can be used.

It is to be understood that in the illustrations of FIGS. 2 and 4-10, the lines are depicted as if the patient was not interposed between the light sources and the holder. However, by broken lines in FIGS. 2 and 4, an ideal location of the patient is depicted. It is desired that the holder 2 and the width of the light beam 10 and 18 are all chosen such that the light beams extend beyond the sides of the patient and impinge upon portions of the holder extending beyond the sides of the patient.

Although the teachings of my invention have herein been discussed with reference to specific theories and embodiments, it is to be understood that these are by way of illustration only and that others may wish to utilize my invention in different designs or applications.

I claim as my invention:

1. In an X-ray photographic device having an X-ray tube received in a housing emitting an X-ray beam through a limiting primary diaphragm received in a diaphragm housing and an independent moveable film holder, a light projecting source fixedly positioned relative to the X-ray beam and adopted to be projected onto markings on the holder for positioning of the holder relative to the housing, the improvement of at least two light beam sources, a first beam source projecting a light beam aligned with the X-ray beam, a second beam source carried in spaced relation to the X-ray source and projecting a light beam at an adjustable angle to the light beam projected by the first light source, the light beams intersecting at a given point spaced from the X-ray source and aligned with the X-ray beam, and markings on the holder being alignable with the point of intersection of the light beams.

2. A device according to claim 1 wherein the second light source produces a bar-shaped light beam projectable beyond the width of a patient lying on the film holder.

3. A device according to claim 2 wherein the bar-shaped light beam is produced in two spaced apart portions.

4. A device according to claim 3 wherein each portion is produced by a separate light source.

5. A device according to claim 4 wherein the separate light sources are positioned on opposite sides of the X-ray housing.

6. A device according to claim 2 wherein the beam produced by the first light source includes a cross-shaped light mark.

7. A device according to claim 6 wherein the cross-shaped light mark is produced by projecting the beam with a first light source through a transparent plate having an opaque cross-shaped mark thereon whereby the beam projecting from the plate has a cross-shaped shadow.

8. A device according to claim 7 wherein the point of intersection of the cross-shaped shadow is substantially aligned with a central axis of the X-ray beam.

9. A device according to claim 8 wherein one of the cross bars of the shadow extends beyond the sides of a patient lying on the film holder.

10. A device according to claim 1 wherein the light beam from the first light source includes a cross-shaped shadow, the point of intersection of the shadow being substantially aligned with the central axis of the X-ray beam, the second light beam including spaced apart substantially rectangular cross-section light bars, the light bars being alignable at a point of intersection of the light beams with a cross bar of the shadow, the film holder including markings thereon extending outwardly from a central film area, the intersected light beams being alignable with the holder markings to indicate proper setting of the film of focus distance by arranging the point of intersection of the light beams on the surface of the holder and further indicating alignment of the X-ray beam with the film by aligning the shadow line of the cross marking with the markings on the holder.

11. A device according to claim 1 wherein the second light source is adjustable relative to the first light source to change the angle of incidence of the light beams.

12. In an X-ray photographic apparatus having an X-ray tube projecting an X-ray beam therefrom, and an independently moveable film holder against which the beam is to project, the improvement of means for setting the film to X-ray focus distance, the said means including a first light source emanating a first light beam, the first light beam aligned with the axis of the X-ray beam, a second light source spaced from the first light source, optics for the second light source, a light beam emanating from the second light source projecting at an adjustable angle to the light beam from the first light source and intersecting therewith at a point spaced from the X-ray source, the point of intersection being projectable on a surface of the film holder indicating achievement of a proper film to focus distance.

13. A device of claim 12 wherein the second light source includes two light sources each projecting a separate light beam, the two light sources positioned with respect to one another such that their intersection with the beam of the first light source is at a common distance from the X-ray source.

14. The device of claim 13 wherein the beam from the first light source includes a shadow marking therein including at least one marking line extending beyond the width of a patient lying on the film holder, the light beam from the second light source being formed as a light bar extending beyond the side of a patient lying on the film holder, intersection of the cross line with the light bar on a surface of a film holder indicating proper positioning of the film holder with respect to the X-ray source, and a center of the shadow marking being aligned with the central axis of the X-ray beam.

15. The device of claim 14 wherein the film holder includes markings projecting centrally from a film area thereof outwardly beyond the width of a patient positioned on the film holder, alignment of the shadow of the beam from the first light source with the markings on the holder indicating central positioning of the X-ray beam with respect to the film carried by the holder.

16. A device according to claim 10 wherein the second light source is adjustable relative to the first light source to change the angle of incidence of the light beams.

17. A device according to claim 15 wherein the shadow is cross-shaped.

* * * * *